United States Patent [19]

Umezawa et al.

[11] Patent Number: 4,463,171

[45] Date of Patent: Jul. 31, 1984

[54] DERIVATIVES OF MACROLIDE ANTIBIOTICS

[75] Inventors: Hamao Umezawa; Tomio Takeuchi; Kuniaki Tatsuta, all of Tokyo; Tomoyuki Ishikura, Chigasaki; Rokuro Okamoto, Fujisawa; Masao Yamamoto, Fujisawa; Kohki Kiyoshima, Fujisawa, all of Japan

[73] Assignee: Sanraku-Ocean Co., Ltd., Tokyo, Japan

[21] Appl. No.: 502,480

[22] Filed: Jun. 9, 1983

[30] Foreign Application Priority Data

Jun. 15, 1982 [JP] Japan ................................ 57-101462

[51] Int. Cl.³ .............................................. C07H 17/08
[52] U.S. Cl. ..................................... 536/7.1; 424/180
[58] Field of Search ........................ 536/7.1; 424/180

[56] References Cited

U.S. PATENT DOCUMENTS 4,396,613  8/1983  Kirst .................................... 536/7.1

FOREIGN PATENT DOCUMENTS 2081711  7/1981  United Kingdom ................ 536/7.1

Primary Examiner—Johnnie R. Brown
Assistant Examiner—Elli Peselev
Attorney, Agent, or Firm—James J. Ralabate

[57] ABSTRACT

Compounds of the following general formula

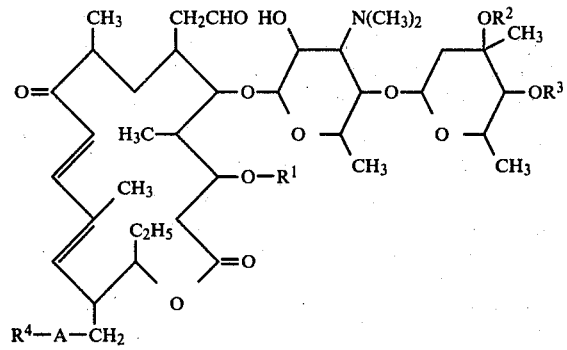

wherein
$R^1$ and $R^2$ represent a hydrogen atom or a lower alkanoyl group;
$R^3$ represents a hydrogen atom or the group —COCH$_2$R$^5$ in which R$^5$ represents a lower alkyl group or an aryl or pyridyl group bonded through a sulfur atom;
$R^4$ represents a methyl group which may be substituted by aryl, pyridyl, pyridylthio, hydroxyl or arylthioamino, an aryl group, a nitrile group, a 5- or 6-membered heterocyclic group having 1 to 4 hetero atoms selected from nitrogen and sulfur atoms, or a tetrahydropyranyl group which may be substituted by methoxy;
A represents the group —OCO—, —OSO$_2$—, —O— or —S—, or A and R$^4$, taken together, represent a halogen atom, a nitrile group or a group of the formula

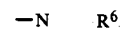

in which R$^6$ represents two lower alkyl groups, the group

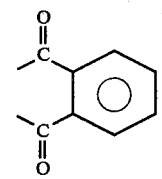

or an alkylene group having 4 to 6 carbon atoms which may have in the chain an oxygen atom or a lower alkyl-substituted nitrogen atom; and said aryl group and heterocyclic group may optionally be substituted by a methyl, methoxy or nitro group, and when $R^1$ represents a lower alkyl group,
$R^3$ does not represent a lower alkyl group,
or their salts.

These novel derivatives of macrolide antibiotics have excellent antibacterial activity.

7 Claims, No Drawings

DERIVATIVES OF MACROLIDE ANTIBIOTICS

FIELD OF THE INVENTION

This invention relates to novel derivatives of macrolide antibiotics. More particularly, it pertains to derivatives having excellent antibacterial activity and derived from N-1 substance or its analog, antibiotic YO-9010, which were previously developed by the present inventors.

BACKGROUND OF THE INVENTION

Many substances such as tylosin, carbomycin, leucomycin and rosamicin are known as 16-membered macrolide antibiotics. Of these, tylosin is one of the oldest 16-membered macrolide antibiotics. Tylosin itself shows high antibacterial activity in vitro. But since its absorbability and excretability in vivo are low, much work has been done for the preparation of tylosin derivatives having excellent absorbability and excretability by chemical or biological converting methods.

From a different standpoint from prior studies, the present inventors have made investigations in order to search for novel analogous compounds of tylosin. When they cultivated a bacterial strain belonging to the genus Streptomyces having the ability of bond mycarose to the hydroxyl group at the 4'-position of the mycaminose of mycaminosyl tylonolide, acetylate the hydroxyl group at the 3-position of the tylonolide and further isovalerylate the hydroxyl group at the 4''-position of mycarose in a nutrient medium containing mycaminosyl tylonolide as a substrate, they obtained 2'-O-acetyl-4''-O-isovaleryl-23-demycinosyl-tylosin which is a compound corresponding to $R^{1-1}$=acetyl and $R^{3-1}$=isovaleryl in the following formula

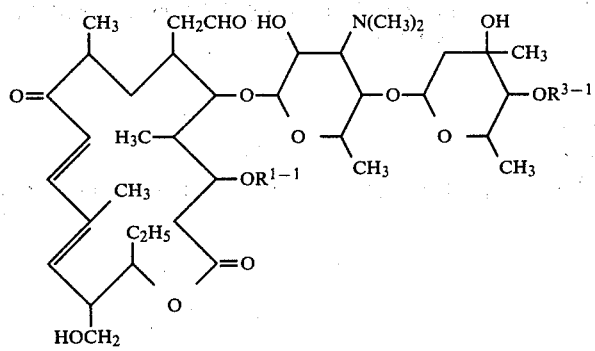

wherein
$R^{1-1}$ represents a hydrogen atom or an acetyl group and
$R^{3-1}$ represents a hydrogen atom or an isovaleryl group.

The present inventors named this compound "N-1 substance," and applied it for a patent (Japanese Laid-Open Patent Publication No. 43013/1980).

The present inventors also made investigations in order to mutate *Streptomyces fradiae* (NRRL B-2702 strain), which is a tylosin-producing strain, under various conditions. When the *Streptomyces fradiae* NRRL B-2702 was mutated by using N-methyl-N'-nitro-N-nitrosoguanidine as a mutation inducing agent and the resulting novel mutant, *Streptomyces fradiae* YO-9010, was cultivated in a nutrient medium, a compound of the above formula (I-a) in which $R^{1-1}$ is a hydrogen atom and $R^{3-1}$ is a hydrogen atom (23-demycinosyltylosin) with the elimination of the mysinose residue bonded to the carbon atom at the 23-position was obtained from the culture broth. The present inventors named this compound "antibiotic YO-9010", and applied it for a patent (Japanese Patent Application No. 44127/1981). The above compound and its lower alkyl ester derivatives were developed independently of the present inventors and recently disclosed (U.S. Pat. No. 4,321,361).

DETAILED DESCRIPTION OF THE INVENTION

This invention relates to a compound of the following general formula

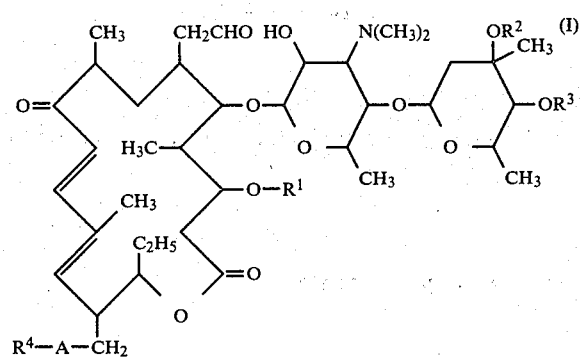

wherein
$R^1$ and $R^2$ represents a hydrogen atom or a lower alkanoyl group;
$R^3$ represents a hydrogen atom or the group —COCH$_2$R$^5$ in which $R^5$ represents a lower alkyl group or an aryl or pyridyl group bonded through a sulfur atom;
$R^4$ represents a methyl group which may be substituted by aryl, pyridyl, pyridylthio, hydroxyl or arylthioamio, an aryl group, a nitrile group, a 5- or 6-membered heterocyclic group having 1 to 4 hetero atoms selected from nitrogen and sulfur atoms, or a tetrahydropyranyl group which may be substituted by methoxy;
A represents the group —OCO—, —OSO—$_2$—, —O— or —S—, or A and $R^4$, taken together, represent a hydrogen atom, a nitrile group or a group of the formula

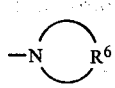

in which $R^6$ represents two lower alkyl groups, the group

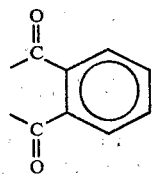

or an alkylene group having 4 to 6 carbon atoms which may have in the chain an oxygen atom or a lower alkyl-substituted nitrogen atom; and said aryl group and heterocyclic group may optionally be substituted by a methyl, methoxy or nitro group, and when $R^1$ represents a lower alkyl group, $R^3$ does not represent a lower alkyl group;

or a salt thereof.

The compounds of formula (I) or the salts thereof provided by this invention, processes for production thereof, and medical uses of these compounds will be described below in detail.

The term "lower," as used herein, means that a group or compound qualified by this term has not more than 6, preferably not more than 4, carbon atoms.

The term "lower alkanoyl group," as used herein, denotes a lower alkylcarbonyl group in which the lower alkyl moiety is linear or branched, and includes, for example, acetyl, propionyl, n-butyryl, isobutyryl, n-valeryl, isovaleryl, and n-caproyl.

A hydrogen atom or an acetyl group is especially preferred as $R^1$ and/or $R^2$ in formula (I) above.

In the definition of $R^3$, the term "lower alkyl group" for $R^5$ in the group $-COCH_2R^5$ has a similar meaning to the above. The "aryl group" in the "aryl or pyridyl group bonded through a sulfur atom" may be mononuclear or polynuclear, and may have at least one, preferably only one, substituent selected from methyl, methoxy and nitro groups on the aromatic ring. Examples of such substituted or unsubstituted aryl groups are phenyl, p-tolyl, o-tolyl, m-tolyl, p-methoxyphenyl, m-methoxyphenyl, o-methoxyphenyl, 3,4,5-trimethoxyphenyl, p-nitrophenyl, m-nitrophenyl, α-naphthyl and β-naphthyl. Of these, phenyl, tolyl and nitrophenyl are especially suitable.

The "pyridyl group" includes 4-pyridyl and 2-pyridyl.

A hydrogen atom, an isovaleryl group, a phenylthioacetyl group and a 4-pyridylthioacetyl group are preferred as $R^3$ in formula (I).

The "aryl group" used in the definition of $R^4$, i.e. "a methyl group which may be substituted by aryl, pyridyl, pyridylthio, hydroxyl or arylthioamino, an aryl group, a nitrile group, a 5- or 6-membered heterocyclic group having 1 to 4 hetero atoms selected from nitrogen and sulfur atoms, or a tetrahydropyranyl group which may be substituted by methoxy", has the same meaning as given above in the explanation of the definition of $R^3$. The "5- or 6-membered heterocyclic group having 1 to 4 hetero atoms selected from nitrogen and sulfur atoms" may be alicyclic or aromatic. Only one kind, or two kinds, of the hetero atoms may exist. The heterocyclic group may have on the nucleus at least one substituent selected from methyl, methoxy and nitro groups, preferably only one methyl group. These groups may be bonded to any one of $-OCO-$, $-OSO_2-$, $-O-$ and $-S-$ defined for A. Preferred examples are a combination of the group $-OCO-$ with an aryl group or a methyl group which is substituted by one group selected from aryl, pyridyl, pyridylthio and arylthioamino groups, or together has one hydroxyl group as a substituent; a combination of the group $-OSO_2-$ with an aryl group; a combination of the group $-O-$ with a methyl group or a tetrahydropyranyl group which may be substituted by methoxy; and a combination of the group $-S-$ with a methyl group, an aryl group, or a 5- or 6-membered heterocyclic group having 1 to 4 hetero atoms selected from nitrogen and sulfur atoms which has on the nucleus at least one substituent selected from methyl, methoxy and nitro groups. Specific examples of the heterocyclic group are shown below.

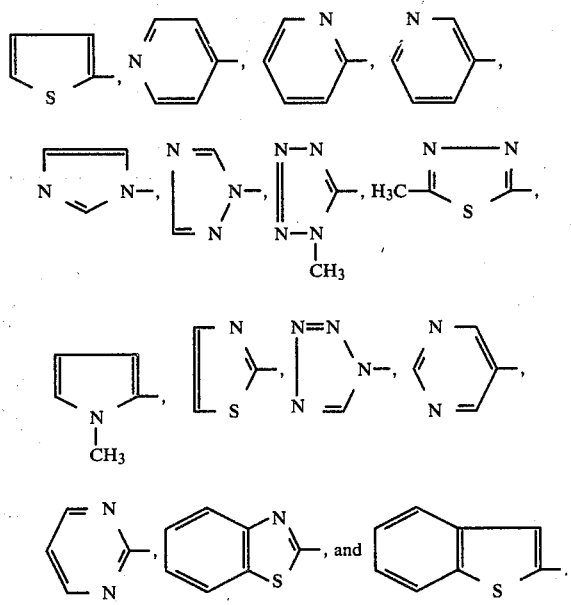

Preferred heterocyclic groups are as follows:

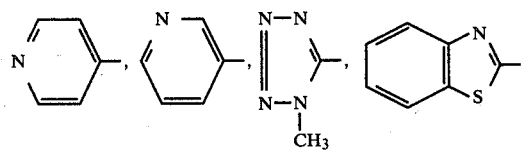

Furthermore, in formula (I), examples of preferred groups represented by a combination of A and $R^4$ are an iodine atom, a bromine atom and a nitrile group. A and $R^4$ taken together also represent a group of the formula

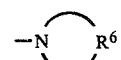

in which $R^6$ represents two lower alkyl groups, or an alkylene group having 4 to 6 carbon atoms which may have in the chain an oxygen atom or a lower alkyl-substituted nitrogen atom. Specific examples of the group are shown below.

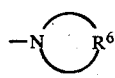

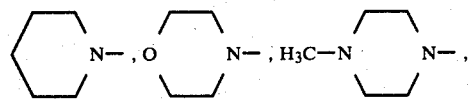

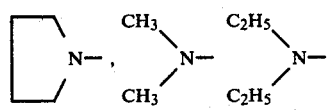

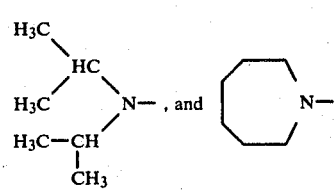

Especially preferred are the following groups.

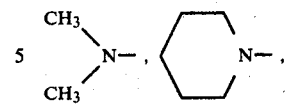

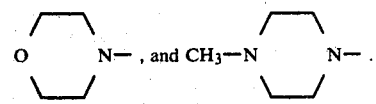

Among the compounds of formula (I) provided by this invention, the most suitable group of compounds are those of formula (I) in which $R^1$ and $R^2$ are hydrogen atoms, $R^3$ represents a hydrogen atom or an isovaleryl group, and the group $R^4$—A represents an iodine or bromine atom. These compounds are noteworthy because they have higher antibacterial activity against pathogenic microorganisms belonging to Gram-negative bacteria than the starting compounds and can be intermediates for synthesis of the other compounds of formula (I).

Typical examples of the compounds of formula (I) provided by this invention are listed below.

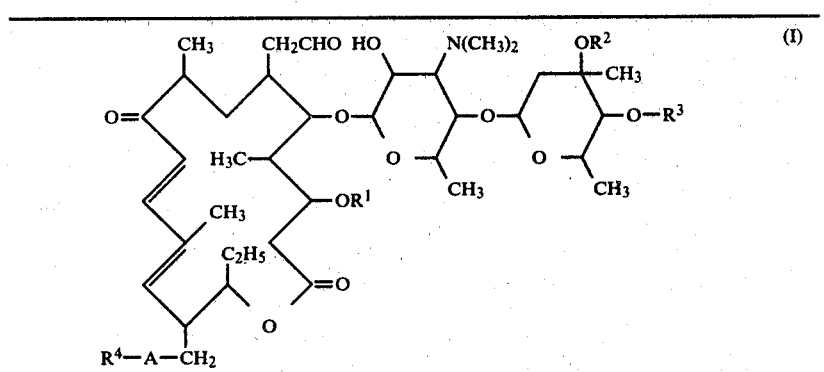

| Compound No. | $R^1$ | $R^2$ | $R^3$ | $R^4$A |
|---|---|---|---|---|
| 1 | H | H | H | Br |
| 2 | " | " | " | I |
| 3 | " | " | " | Cl |
| 4 | COCH$_3$ | " | " | Br |
| 5 | " | " | " | I |
| 6 | H | " | COCH$_2$CH(CH$_3$)$_2$ | Br |
| 7 | " | " | " | I |
| 8 | COCH$_3$ | " | " | Br |
| 9 | " | " | " | I |
| 10 | H | " | H | 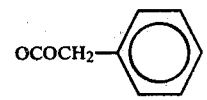 |
| 11 | " | " | " | 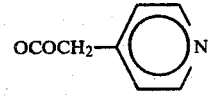 |
| 12 | " | " | " | 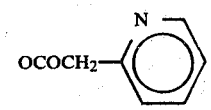 |

-continued
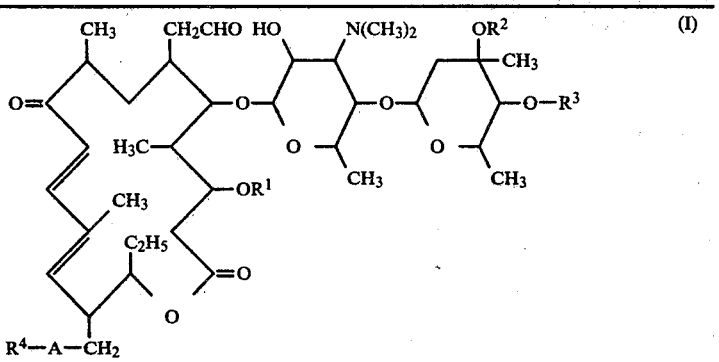
| Compound No. | R¹ | R² | R³ | R⁴A |
|---|---|---|---|---|
| 13 | " | " | " | OCOCH₂-（2-thienyl） |
| 14 | " | " | " | OCOCH(OH)-phenyl |
| 15 | " | " | " | OCOCH(phenyl)-NHS-（2-nitrophenyl） |
| 16 | " | " | " | OCOCH₂-S-（4-pyridyl） |
| 17 | " | " | " | OCO-phenyl |
| 18 | " | " | " | OCO-（3,4,5-trimethoxyphenyl） |
| 19 | " | " | " | OCOCH₂-（1-methyl-2-pyrrolyl） |
| 20 | " | " | " | OCOCH₂-（2-thiazolyl） |
| 21 | " | " | " | OCOCH₂-N（1,2,3,4-tetrazolyl） |

-continued
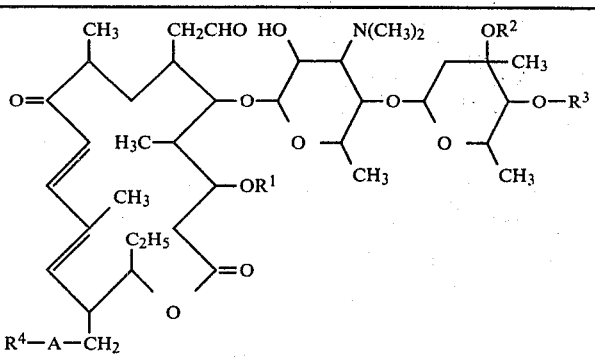
| Compound No. | R¹ | R² | R³ | R⁴A |
|---|---|---|---|---|
| 22 | " | " | " | S—CH₃ |
| 23 | " | " | " | S—C₆H₅ |
| 24 | " | " | " | S-C(=N-N=N-NCH₃) (1-methyltetrazol-5-ylthio) |
| 25 | " | " | " | S-(benzothiazol-2-yl) |
| 26 | " | " | " | S—CH₂CH₃ |
| 27 | " | " | " | S—CH₂CH₂N(CH₃)₂ |
| 28 | " | " | " | S—CH₂CH₂OH |
| 29 | COCH₃ | " | " | S—CH₂CH₂CH₃ |
| 30 | H | " | COCH₂CH(CH₃)₂ | S—CH₂C₆H₅ |
| 31 | " | " | " | S-(5-methyl-1,3,4-thiadiazol-2-yl) |
| 32 | " | " | " | S-(pyridin-4-yl) |
| 33 | COCH₃ | " | " | S-(pyridin-2-yl) |
| 34 | " | " | " | S-(thiazol-2-yl) |
| 35 | " | " | " | S—C₆H₅ |
| 36 | " | " | " | S—CH₃ |

-continued

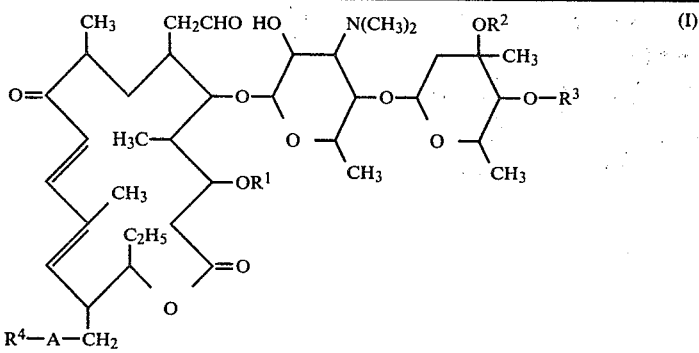

| Compound No. | $R^1$ | $R^2$ | $R^3$ | $R^4A$ |
|---|---|---|---|---|
| 37 | " | " | " | S—CH$_2$CH$_2$N(CH$_3$)$_2$ |
| 38 | H | " | H | OCH$_3$ |
| 39 | " | " | " | OCH$_2$CH$_3$ |
| 40 | " | " | " | OCH$_2$CH$_2$CH$_3$ |
| 41 | " | " | " | OCH$_2$C(=O)CH$_3$ |
| 42 | " | " | " | OCH$_2$C(=O)CH$_2$CH$_3$ |
| 43 | " | " | " | OCH$_2$—C$_6$H$_5$ |
| 44 | " | " | " | OCH$_2$C(=O)—C$_6$H$_5$ |
| 45 | COCH$_3$ | " | " | OCH$_2$CH(CH$_3$)$_2$ |
| 46 | H | " | COCH$_2$CH(CH$_3$)$_2$ | OCH$_3$ |
| 47 | " | " | " | O—cyclohexyl |
| 48 | " | " | " | O—cyclopentyl |
| 49 | " | " | " | O—cycloheptyl |
| 50 | COCH$_3$ | " | " | OCH$_3$ |
| 51 | " | " | " | OCH$_2$CH$_3$ |
| 52 | " | " | " | OCH(CH$_3$)$_2$ |
| 53 | " | " | " | OCH$_2$CH$_2$CH$_2$CH$_3$ |
| 54 | " | " | " | OCH$_2$—cyclohexyl |

-continued
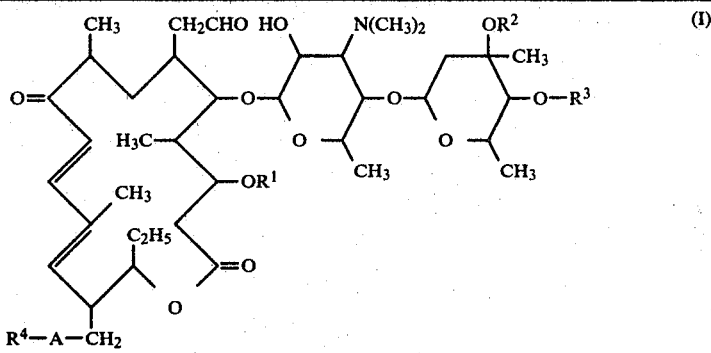
| Compound No. | R¹ | R² | R³ | R⁴A |
|---|---|---|---|---|
| 55 | " | " | " | OCH₂—C₆H₅ |
| 56 | " | " | " | OCH₂—C(O)—C₆H₅ |
| 57 | H | " | H | tetrahydropyran-2-yloxy |
| 58 | " | " | " | tetrahydrofuran-2-yloxy |
| 59 | " | " | " | 6-methoxy-tetrahydropyran-2-yloxy |
| 60 | COCH₃ | " | COCH₂CH(CH₃)₂ | tetrahydropyran-2-yloxy |
| 61 | H | " | H | $N(CH_3)_2$ |
| 62 | " | " | " | $N(CH_2CH_3)_2$ |
| 63 | " | " | " | $N(CH_2CH_2CH_3)_2$ |
| 64 | " | " | " | pyrrolidin-1-yl |
| 65 | " | " | " | piperidin-1-yl |
| 66 | " | " | " | hexahydroazepin-1-yl |

-continued
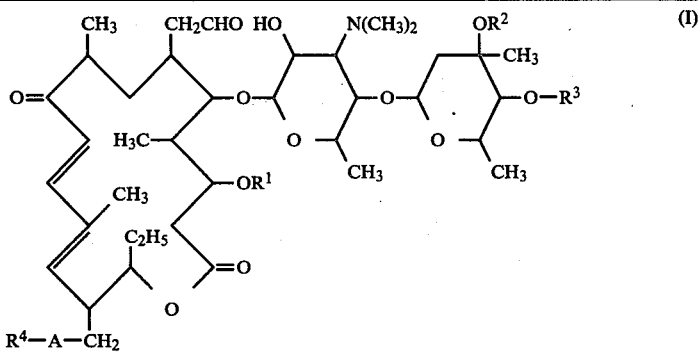
| Compound No. | R¹ | R² | R³ | R⁴A |
|---|---|---|---|---|
| 67 | " | " | " | ![morpholino] N⌒O |
| 68 | " | " | " | N-methylpiperazino |
| 69 | COCH₃ | " | " | N(CH₃)₂ |
| 70 | H | " | COCH₂CH(CH₃)₂ | N(CH(CH₃)₂)₂ |
| 71 | COCH₃ | " | " | N(CH₃)₂ |
| 72 | " | " | " | piperidino |
| 73 | " | " | " | N-methylpiperazino |
| 74 | " | " | " | morpholino |
| 75 | H | " | H | phthalimido |
| 76 | " | " | " | 4-methyl-2,3-dioxopiperazino |
| 77 | " | " | " | SCN |
| 78 | " | " | " | CN |
| 79 | COCH₃ | " | COCH₂CH(CH₃)₂ | SCN |
| 80 | H | " | COCH₂S-C₆H₅ | Br |

-continued

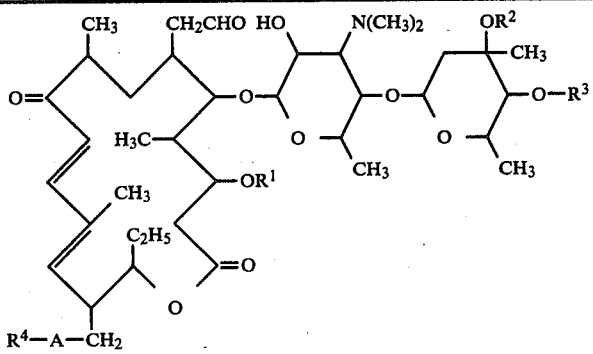
(I)

| Compound No. | R¹ | R² | R³ | R⁴A |
|---|---|---|---|---|
| 81 | " | " | COCH₂S—⟨pyridin-4-yl⟩ | Br |
| 82 | COCH₃ | COCH₃ | COCH₂CH(CH₃)₂ | OH |
| 83 | H | " | " | OH |
| 84 | " | " | " | OCOCH₃ |
| 85 | " | " | OCOCH₂—⟨pyridin-3-yl⟩ | OH |
| 86 | COCH₃ | " | COCH₃ | OH |
| 87 | H | COCH₂CH₃ | COCH₂CH(CH₃)₂ | OH |

The compounds of formula (I) can exist in the form of acid addition salts because they have a basic amino group in the molecule. Acids which can be used to form the acid addition salts include inorganic acids such as hydrochloric acid, sulfuric acid and phosphoric acid and organic acids such as acetic acid, tartaric acid, propionic acid, citric acid and succinic acid.

The compounds of formula (I) can be produced by various processes described below depending upon the types of substituents.

For example, a compound of formula (I) in which A and R⁴, taken together, represent a halogen atom can be produced by protecting the hydroxyl groups at the 3- and/or 2'-position of the compound of formula (I-a), halogenating the carbon atom at the 23-position by a halogenating method known per se and thereafter eliminating the protective groups at the 3- and 2'-positions; or by halogenating the carbon atom at the 23-position by a method which enables only the primary hydroxyl group to be halogenated. More specifically, this process is carried out by reacting a halogenating agent generally at a temperature of from about −30° C. to the refluxing temperature of the reaction mixture, preferably about 0° C. to about 60° C., in the absence of a solvent, or in the presence of a suitable inert solvent such as methylene chloride, chloroform, carbon tetrachloride, tetrachloroethane, diethyl ether, tetrahydrofuran (to be referred to as "THF"), dimethylformamide (to be referred to as "DMF"), acetonitrile, dimethyl sulfoxide (to be referred to as "DMSO"), and acetone. Examples of the halogenating agent include thionyl chloride, thionyl bromide, phosphorus tribromide, phosphorus pentabromide, bromine, methyl iodide, bromonitrile, N-bromosuccinimide (to be referred to as "NBS"), carbon tetrachloride and carbon tetrabromide. As required, the reaction can be carried out in the further presence of a reaction promoter such as pyridine, triphenylphosphine, triphenoxyphosphine, and tridimethylaminophosphine either alone or in combination.

In the present invention, it is desirable to use at least one reagent selected from carbon tetrachloride, bromine, NBS, carbon tetrabromide, thionyl chloride, triphenylphosphine iodine and methyl iodide as the halogenating agent in the co-presence of triphenylphosphine or triphenoxyphosphine dissolved in pyridine as the reaction promoter and if required, use pyridine, DMF, acetonitrile, etc. as the solvent.

The amount of the halogenating agent such as carbon tetrabromide used in the above reaction is not strictly limited. Generally, it can be used in an amount of 1 to 5 moles, preferably 1 to 3 moles, per mole of the compound of formula (I-a) or a compound resulting from the protection of its hydroxyl groups at the 3-position and/or 2'-position. When triphenylphosphine is to be used as the promoter in this reaction, it is convenient to add it as a 0.1M–5M pyridine solution in an amount of 1 to 10 moles, preferably 1 to 5 moles, per mole of the starting macrolide antibiotic.

A compound of formula (I) in which R⁴ is a methyl group which may be substituted by aryl, pyridyl, pyridylthio, hydroxyl or arylthioamino, an aryl group, a nitrile group, a 5- or 6-membered heterocyclic group having 1 to 4 hetero atoms selected from nitrogen and sulfur atoms, or a tetrahydropyranyl group which may be substituted by methoxy and A represents the group —OCO— or —S— can be produced by reacting a compound of the following formula obtained by the aforesaid process

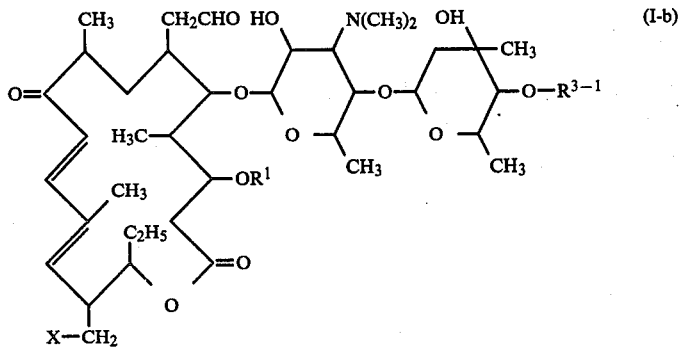

wherein
R[1] and R[3-1] are as defined above and
X represents a halogen atom,
or a salt thereof, with a reactive derivative represented by the following formula $$R^4—A'—Y \quad (II)$$

wherein
R[4] is as defined above;
A' represents the group —OCO— or —S—;
R[4] and A' taken together represent a nitrile group or a group of the formula

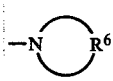

in which R[6] is as defined; and
Y represents a hydrogen, sodium or potassium atom, to substitute the halogen atom bonded to the carbon atom at the 23-position of the compound of formula (I-b) by the group R[4]—A', and as required, acylating the hydroxyl group at the 4"-position.

The reaction of substituting the group R[4]—A' for the halogen atom can be carried out in accordance with a dehydrohalogenation reaction or desalting reaction known per se. The reaction can be carried out generally at about −30° C. to about 60° C., preferably −10° C. to 60° C., in an inert solvent such as DMF, THF, acetonitrile, acetone or DMSO, as required in the presence of sodium iodide or an amine such as pyridine or triethylamine as a reaction promoter.

A compound of formula (I) in which R[4] in the group R[4]—A represents a tetrahydropyranyl group which may be substituted by methoxy can be produced by dissolving the aforesaid N-1 substance or antibiotic YO-9010 in an inert solvent such as methylene chloride or THF, subjecting the solution to a known reaction of tetrahydropyranylating the hydroxyl group in the presence of a pyranylating agent capable of converting the hydroxyl group to tetrahydropyran-2-yl, such as 2,3-dihydro-4H-pyran, a 2-halotetrahydropyran or a 2-acyloxy-tetraydropyran and as a reaction promoter, an organic acid such as trifluoroacetic acid or p-toluenesulfonic acid, and as required, acylating the hydroxyl group at the 3- and/or 4"-position. Preferably, the reaction is carried out by using methylene chloride as the inert solvent, 2,3-dihydro-4H-pyran as the tetrahydropyranylating agent and an organic acid such as trifluoroacetic acid as the reaction promoter at a reaction temperature of −20° C. to 30° C., preferably −10° C. to room temperature, for 24 to 48 hours. The amount of the tetrahydropyranylating agent is not particularly restricted. But to tetrahydropyranylate the hydroxyl group on the carbon atom at the 23-position selectively, the amount of the tetrahydropyranylating agent is desirably 1 to 5 moles, preferably 1 to 3 moles, per mole of the starting N-1 substance or antibiotic YO-9010. The suitable amount of the reaction promoter used in the reaction varies with its type. When trifluoroacetic acid is used, its amount is preferably 1 to 3 moles per mole of the starting antibiotic.

Processes for producing compounds of formula (I) in which A in the group R[4]—A is —OSO$_2$—, or compounds of formula (I) in which A is —OCO—, other than those described above, and the optional acylation of the hydroxyl group at the 3- and/or 4"-position can be performed in accordance with known methods ordinarily used in the technological field of synthesizing derivatives of macrolide antibiotics (see, for example, U.S. Pat. No. 4,205,163).

The compounds of formula (I) produced as above can be converted to their acid addition salts by treating them with hydrochloric acid, phosphoric acid, sulfuric acid, tartaric acid, succinic acid, propionic acid, citric acid, etc. by methods known per se.

The compounds of formula (I) and their salts provided by this invention have strong antibacterial activity against pathogenic microorganisms such as various Gram-positive bacteria, Gram-negative bacteria and mycoplasma, and exhibit excellent bioavailability. Their high activity can be demonstrated by the following tests.

(1) Antibacterial activity

The antibacterial activities of some typical compounds of this invention were measured by a tube dilution method in a brain heart infusion broth (pH 7.5) as a culture medium. The results are shown in Table 1 below.

TABLE 1
Antibacterial activity
(minimum inhibitory concentration, mcg/ml)

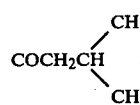

| $R^1$ ($R^2$)* | $R^3$ | A—$R^4$ | *Staphylococcus aureus* 209P | *Staphylococcus aureus* MS9861 | *Bacillus subtilis* NRRL B558 | *Klebsiella pneumoniae* PCI602 |
|---|---|---|---|---|---|---|
| H | H | OH** | 0.8 | 3.1 | 1.6 | 12.5 |
| " | COCH$_2$CH(CH$_3$)$_2$ | " | 0.4 | 1.6 | 0.8 | 1.6 |
| COCH$_3$ (COCH$_3$) | " | OH*** | 0.4 | 1.6 | 0.8 | 3.1 |
|  | " | " | 0.8 | 3.1 | 0.4 | >100 |
| H | COCH$_2$—S—C$_6$H$_5$ | " | 0.4 | 3.1 | <0.2 | 3.1 |
| " | COCH$_3$ | " | 1.6 | 25 | 1.6 | 3.1 |
| " | H | Br | <0.2 | 0.8 | <0.2 | 6.3 |
| " | " | I | 0.4 | 3.1 | <0.2 | 6.3 |
| " | COCH$_2$CH(CH$_3$)$_2$ | Br | 0.8 | 1.6 | 0.4 | 6.3 |
| COCH$_3$ | " | " | 1.6 | 3.1 | 1.6 | >100 |
| H | COCH$_2$—S—C$_6$H$_5$ | " | 0.4 | 3.1 | 1.6 | >100 |
| " | COCH$_2$—S—(pyridyl) | " | 0.2 | 0.8 | <0.2 | 12.5 |
| " | H | OCOCH$_3$ | 0.4 | 1.6 | 0.4 | 25 |
| " | " | OCOCH$_2$—C$_6$H$_5$ | 0.4 | 1.6 | <0.2 | 6.3 |
| " | " | " | 0.4 | 3.1 | 0.4 | 6.3 |
| " | " | OCOCH$_2$—S—(pyridyl) | 0.8 | 3.1 | <0.2 | 12.5 |

TABLE 1-continued

Antibacterial activity
(minimum inhibitory concentration, mcg/ml)

[Structure: macrolide antibiotic with substituents $OR^1$, $OR^2$, $OR^3$, and $R^4-A-CH_2$ group, containing $CH_3$, $CH_2CHO$, HO, $N(CH_3)_2$, $C_2H_5$ groups]

| $R^1$ ($R^2$)* | $R^3$ | A—$R^4$ | Staphylococcus aureus 209P | Staphylococcus aureus MS9861 | Bacillus subtilis NRRL B558 | Klebsiella pneumoniae PCI602 |
|---|---|---|---|---|---|---|
| " | " | OCOCH(OH)—C₆H₅ | 0.4 | 1.6 | <0.2 | 12.5 |
| " | " | OCOCH(NHS-C₆H₄-o-NO₂)—C₆H₅ | 0.8 | 3.1 | 0.8 | 3.1 |
| " | COCH₂CH(CH₃)₂ | OCOCH₃ | 0.8 | 6.3 | 1.6 | 3.1 |
| (COCH₃) | " | " | 1.6 | 6.3 | 1.6 | 25 |
| H | COCH₂—S—C₆H₅ | " | 0.8 | 1.6 | 0.2 | 100 |
| " | COCH₂CH(CH₃)₂ | OCOCH₂CH(CH₃)₂ | 1.6 | 12.5 | 0.8 | 6.3 |
| " | H | OSO₂—C₆H₄—CH₃ | 0.8 | 6.3 | 0.4 | 25 |
| " | " | S—C₆H₅ | <0.2 | 1.6 | <0.2 | 25 |
| " | " | S—(1-methyl-tetrazol-5-yl) | 0.8 | 3.1 | <0.2 | 12.5 |

TABLE 1-continued

Antibacterial activity
(minimum inhibitory concentration, mcg/ml)

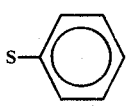

| R¹ (R²)* | R³ | A—R⁴ | Staphylococcus aureus 209P | Staphylococcus aureus MS9861 | Bacillus subtilis NRRL B558 | Klebsiella pneumoniae PCI602 |
|---|---|---|---|---|---|---|
| " | " | SCH₃ | 0.8 | 1.6 | 0.8 | 6.3 |
| " | COCH₂CH(CH₃)CH₃ | S—⟨phenyl⟩ | 3.1 | 6.3 | 3.1 | >100 |
| " | H | O—⟨tetrahydropyran⟩ | 0.8 | 3.1 | 0.8 | 12.5 |

Note:
*The parenthesized description refers to a 3"-hydroxyl substituted derivative.
**Antibiotic YO-9010
***N-1 substance The following Referential Examples illustrate the production of the N-1 substance and the antibiotic YO-9010 used as starting materials for the derivative of this invention. The present invention is further illustrated by the following Examples.

REFERENTIAL EXAMPLE 1

Production of N-1 substance:

One hundred milliliters of a culture medium (pH 7.0) composed of 2 g/dl of glucose, 2 g/dl of soybean meal, 0.1 g/dl of yeast extract, 0.05 g/dl of K₂HPO₄ and 0.05 g/dl of MgSO₄.7H₂O was put in each of 500 ml Erlenmeyer flasks, and sterilized under pressure to give a seed culture medium.

One hundred liters of a culture medium having the same composition as above was put in a 200-liter fermentation tank, and an antifoamer was added in a concentration of 0.05 g/dl. The mixture was sterilized under pressure to give a main culture medium.

One loopful of *Streptomyces thermotolerans* (ATCC 11416) grown on a slant was inoculated in the seed culture medium, and cultivated at 37° C. for 2 days by a rotary shaker. Five such weeds were inoculated in the fermentation tank, and cultivated at 37° C. for about 24 hours with aeration and agitation. After confirming that the microbial cells grew sufficiently, 20 g of mycaminosyl tylonolide dissolved in water was added to the fermentation liquor and subsequently reacted for 20 hours under the same conditions as in the cultivation.

After the reaction, the fermentation broth was adjusted to pH 4.0 with sulfuric acid and filtered by a filter press to obtain about 80 liters of a filtrate. The filtrate was concentrated to 20 liters by a reverse osmosis concentrator. The residue was adjusted to pH 7.0 with sodium hydroxide, and extracted at 37° C. with two 5-liter portions of toluene to transfer the reaction product to 10 liters of the toluene layer. The toluene layer was then concentrated 1 liter under reduced pressure, and mixed with 10 liters of acidic water (pH 3.7) at 5° C. to transfer the reaction product to the aqueous layer. The aqueous layer was adjusted to pH 7.0, and mixed with 1 liter of toluene at 37° C. to transfer the reaction product again to the toluene layer. The toluene layer was concentrated to dryness to give about 10 g of a yellowish brown powder containing the reaction product.

The yellow powder was chromatographed on a silica gel column (5 cm in diameter and 50 cm in length) using a mixture of benzene, acetone and methanol (30:10:1) as an eluent. Eluates mainly containing only the N-1 substance were collected, and concentrated to dryness to give about 3 g of a pale yellow powder containing about 80% of N-1 substance.

The pale yellow powder was again purified under the same conditions as in the aforesaid column chromatography to give about 1.5 g of N-1 substance as a white powder.

REFERENTIAL EXAMPLE 2

Production of antibiotic YO-9010:

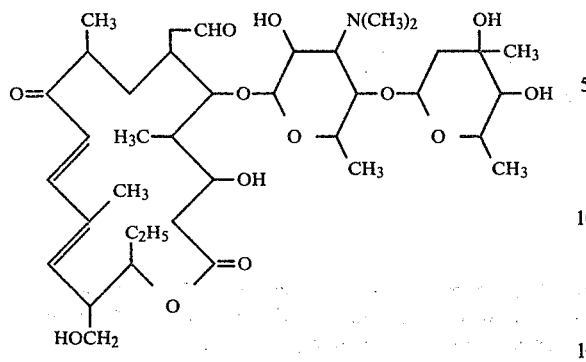

(Except special cases, the macrocyclic lactone portion is abbreviated hereinbelow as

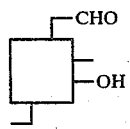

and the antibiotic YO-9010 is referred to simply as "YO-9010".)

(1) Cultivation of *Streptomyces fradiae* YO-9010 strain

One loopful of a grown slant culture of *Streptomyces fradiae* YO-9010 strain (ATCC 31846) was inoculated in a 500 ml Erlenmeyer flask containing 50 ml of a seed culture medium consisting of 1.5% of glycerol, 1% of polypeptone, meat extract, 0.1% of dipottasium phosphate and 0.1% of magnesium sulfate, and cultivated on a rotary shaking fermentor at 30° C. for 2 days. The seed culture broth was inoculated in a 20-liter jar fermentor containing 10 liters of a production medium consisting of 6% of soluble starch, 2% of dry yeast, 0.1% of yeast extract, 0.1% of dipottasium phosphate, 0.1% of magnesium sulfate, 0.5% of sodium chloride and 0.4% of calcium carbonate, and cultivated at 30° C. for 5 days at an air flow rate of 10 liters/min. and a rotating speed of 350 rpm.

(2) Recovery of antibiotic YO-9010

The cultivation broth obtained in (1) above was collected, and adjusted to pH 8.5 with sodium hydroxide. One liter of toluene was added to extract the cultivation broth with stirring. The toluene layer was recovered by centrifugal separation. The toluene layer was cooled to 5° C., and 200 ml of M/5 sodium acetate/HCl buffer (pH 3.5) was added. The mixture was stirred, and the buffer layer was separated by centrifugal separation. The buffer layer was adjusted to pH 8.5 with sodium hydroxide, and 100 ml of ethyl acetate was added. The mixture was stirred to extract the buffer layer. The separated ethyl acetate layer was concentrated to dryness under reduced pressure. The dried product was washed with a small amount of ether, and dried to give 650 mg of a pale yellowish white powder. The powder was subjected to silica gel thin-layer chromatography to determine the purity of antibiotic YO-9010. It was found to be 91%.

EXAMPLE 1

23-Deoxy-23-bromo-YO-9010

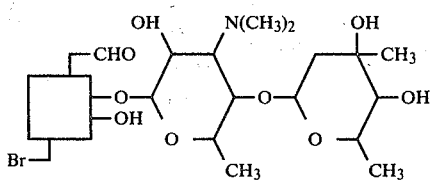

5.0 g of YO-9010 and 5.31 g of triphenylphosphine were dissolved in 50 ml of pyridine, and the solution was cooled with ice. Then, 4.48 g of carbon tetrabromide was added, and the mixture was stirred at 0° C. for 10 minutes and then at room temperature for 1 hour. The reaction was stopped by adding 4 ml of methanol. Pyridine was removed by concentration to dryness. The residue was purified by silica gel column chromatography (CHCl$_3$ and CHCl$_3$/MeOH=30/1) to give 1.94 g of the desired compound.

RF: 0.64 (CHCl$_3$/MeOH=5/1),
Mass: 803 (M+),
$[\alpha]_D^{22}$: −35.7° (c 0.987, MeOH),
UV: $\lambda_{max}^{MeOH}$ 281 nm, $E_{1cm}^{1\%}=269$,
Molecular formula: C$_{38}$H$_{62}$NO$_{12}$Br,
$^1$H-NMR: δ1.82 (3H, s, 12—CH$_3$), 2.47 (6H, s, N(CH$_3$)$_2$), 5.79 (1H, d, H-13), 6.26 (1H, d, H-10), 7.30 (1H, d, H-11), 9.65 (1H, s, CHO).

EXAMPLE 2

23-Deoxy-23-iodo-YO-9010

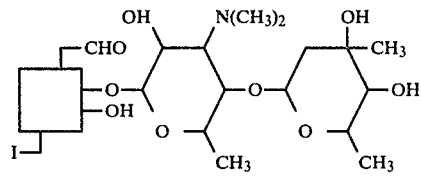

210 mg of 23-deoxy-bromo-YO-9010 was dissolved in 3 ml of acetone, and 8 ml of a 15% acetone solution of NaI was added to the resulting solution. The mixture was stirred at room temperature for 3 hours. The reaction mixture was poured into 50 ml of chloroform, washed with an aqueous solution of sodium bicaronate and an aqueous solution of sodium chloride, and then dried over anhydrous sodium sulfate. The dried product was purified by silica gel column chromatography (benzene/acetone=3/1) to give 202 mg of the desired compound.

Rf: 0.47 (chloroform/methanol=6/1),
Mass: 851 (M+),
$[\alpha]_D^{23}$: −13.1° (c 0.337, MeOH),
UV: $\lambda_{max}^{MeOH}$ 282 nm, $E_{1cm}^{1\%}=252$,
Molecular formula: C$_{38}$H$_{62}$NO$_{12}$I,
$^1$H-NMR: (CDCl$_3$) δ1.81 (3H, s, 12—CH$_3$), 2.47 (6H, s, N(CH$_3$)$_2$), 5.66 (1H, d, H-13), 6.27 (1H, d, H-10), 7.27 (1H, d, H-11), 9.64 (1H, s, CHO).

EXAMPLE 3

3-O-Acetyl-23-deoxy-23-bromo-4''-O-isovaleryl-YO-9010 (23-deoxy-23-bromo-N-1)

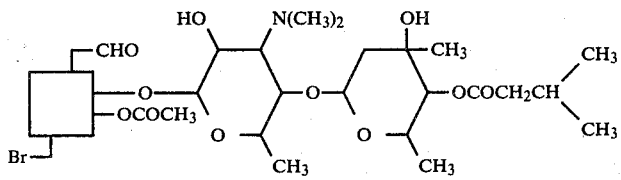

700 mg of N-1 substance, 635 mg of triphenylphosphine and 535 mg of carbon tetrabromide were dissolved in 35 ml of pyridine, and the solution was stirred at room temperature for 30 minutes. The reaction mixture was poured into 100 ml of toluene, washed with an aqueous solution of sodium bicarbonate and an aqueous solution of sodium chloride, and dried over anhydrous sodium sulfate. After filtration, toluene was evaporated under reduced pressure. The residue was purified by Sephadex®LH-20 column chromatography (MeOH) to give 616 mg of the desired compound.

Rf: 0.60 (benzene/acetone=2/1),
Mass: 929 ($M^{30}$),
$[\alpha]_D^{23}$: $-17.3°$ (c 0.237, MeOH),
UV: $\lambda_{max}^{MeOH}$ 282 nm, $E_{1cm}^{1\%}=215$,
NMR(CDCl$_3$): $\delta 0.98$ (6H, d, CH(CH$_3$)$_2$), 1.83 (3H, s, 12—CH$_3$), 2.10 (3H, s, 3—OCOCH$_3$), 2.54 (6H, s, N(CH$_3$)$_2$), 5.83 (1H, d, H-13), 6.26 (1H, d, H-10), 7.36 (1H, d, H-11), 9.59 (1H, s, CHO).

EXAMPLE 4

23-Deoxy-23-bromo-2'-O-acetyl-YO-9010

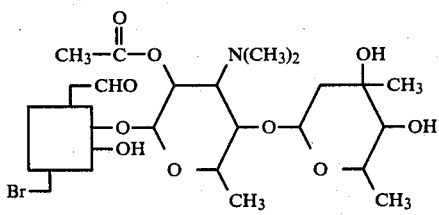

2.74 g of 2'-O-acetyl-YO-9010 (prepared in accordance with Example 8 of the specification of Japanese Laid-Open Patent Publication No. 31699/1982), 2.75 g of triphenylphosphine and 2.32 g of carbon tetrabromide were dissolved in 25 ml of pyridine, and the solution was stirred at 0° C. for 40 minutes, and then at room temperature for 20 minutes. To the reaction mixture was added 5 ml of methanol, and the mixture was further stirred at room temperature for 30 minutes. The solvent was evaporated under reduced pressure, and the residue was purified by silica gel chromatography (chloroform/methanol=80/1) to give 778 mg of the desired compound.

Rf: 0.58 (chloroform/methanol=20/1),
Mass: 845 (M+),
$[\alpha]_D^{23}$: $-47.3°$ (c 0.987, MeOH),
UV: $\lambda_{max}^{MeOH}$ 281 nm, $E_{1cm}^{1\%}=248$,
Molecular formula: C$_{40}$H$_{64}$NO$_{13}$Br,
$^1$H-NMR (CDCl$_3$): $\delta 1.80$ (3H, s, 12—CH$_3$), 2.04 (3H, s, 2'—O—OCOCH$_3$), 2.37 (6H, s, N(CH$_3$)$_2$), 5.78 (1H, d, H-13), 6.29 (1H, d, H-10), 7.29 (1H, d, H-11), 9.65 (1H, s, CHO).

EXAMPLE 5

20,23,2'4''-tetra-O-acetyl-3,20-O-cyclo-YO-9010

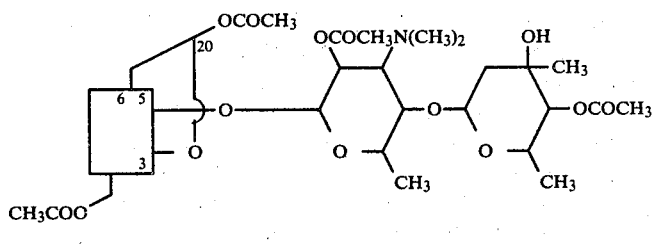

Five grams of YO-9010 was dissolved in 15 ml of acetic anhydride, and 5 g of potassium carbonate was added. The mixture was stirred at 60° C. Seventeen hours later, 5 ml of acetic anhydride was further added, and the mixture was stirred at 60° C. After the lapse of 1.5 hours, the mixture was cooled, and the reaction mixture was poured into 200 ml of water. The pH was adjusted to 9. It was extracted with three 100 ml portions of chloroform. The chloroforms were washed with water and then dried over magnesium sulfate. Chloroform was removed by concentration, and the residue was purified by silica gel column chromatography (benzene/acetone=6/1) to give 1.53 g of the desired compound.

Rf: 0.35 (benzene/acetone=3/1),
Mass: 909 (M+),
$[\alpha]_D^{22}$: $-98.6°$ (c 1, MeOH),
UV: $\lambda_{max}^{MeOH}$ 278 nm, $E_{1cm}^{1\%}=221$,
Molecular formula: C$_{46}$H$_{71}$NO$_{17}$.

EXAMPLE 6

20,23,2',3''-tetra-O-acetyl-4''-O-isovaleryl-3,20-O-cyclo-YO-9010

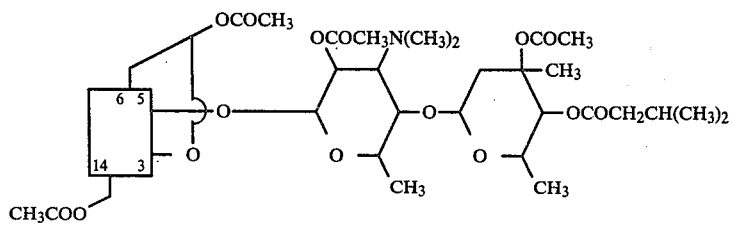

500 mg of 20,23,2′,4″-tetra-O-acetyl-3,20-O-cyclo-YO-9010 was dissolved in 10 ml of dry benzene. Then, 4.4 ml of isovaleric anhydride, 3.04 ml of triethylamine and 67.1 mg of 4-dimethylaminopyridine were added to the solution, and the mixture was heated under reflux for 12.5 hours. After cooling, the reaction mixture was poured into 150 ml of toluene, washed with two 50 ml portions of a saturated aqueous solution of sodium bicarbonate and 50 ml of a saturated aqueous solution of sodium chloride, and then dried over anhydrous sodium sulfate. The anhydrous sodium sulfate was separated by filtration, and toluene was removed by concentration. The residue was purified by silica gel column chromatography (benzene/acetone=12/1 and 11/1) to give 227 mg of the desired compound.

Rf: 0.67 (benzene/acetone=4/1),
Mass: 993 (M+),
$[\alpha]_D^{23}$: −107.7° (c 0.204, MeOH),
UV: $\lambda_{max}^{MeOH}$ 277 nm, $E_{1cm}^{1\%}=236$,
Molecular formula: $C_{51}H_{79}NO_{18}$.

EXAMPLE 7

3″-O-acetyl-4″-O-isovaleryl-YO-9010

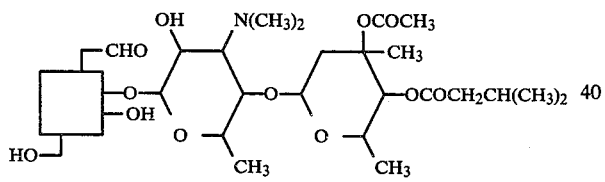

200 mg of 20,23,2′,3″-tetra-O-acetyl-4″-O-isovaleryl-3,20-O-cyclo-YO-9010 was dissolved in 20 ml of methanol, and the solution was heated under reflux for 16 hours. After cooling, methanol was removed by concentration to dryness, and the residue was again dissolved in 40% ammonia-saturated methanol. The solution was stirred at room temperature for 4 hours. The reaction mixture was poured into 50 ml of chloroform, washed with 20 ml of water and 20 ml of an aqueous solution of sodium chloride, and dired over anhydrous sodium sulfate. After filtration, chloroform was removed by concentration, and the residue was purified by silica gel column chromatography (benzene/acetone=4/1) to give 72 g of the desired compound.

Rf: 0.38 (benzene/acetone=2/1),
Mass: 867 (M+),
$[\alpha]_D^{23}$: −58.4° (c 0.197, MeOH),
UV: $\lambda_{max}^{MeOH}$ 283 nm, $E_{1cm}^{1\%}=235$,
Molecular weight: $C_{45}H_{73}NO_{15}$.

EXAMPLE 8

23-Deoxy-23-bromo-2′-O-acetyl-4″-O-isovaleryl-YO-9010

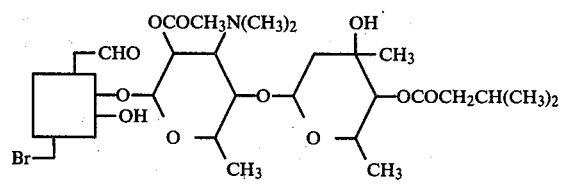

200 mg of 23-deoxy-23-bromo-2′-O-acetyl-YO-9010 was dissolved in 2 ml of pyridine, and 2 ml of isovaleric anhydride was added. The mixture was stirred at 8° C. for 2 days. The reaction mixture was poured into 50 ml of ice water to decompose the excess of isovaleric anhydride. Then, it was extracted with 100 ml of toluene. The toluene layer was washed with two 50 ml portions of sodium bicarbonate and then with an aqueous solution of sodium chloride, and dried over anhydrous sodium sulfate. The solvent was evaporated under reduced pressure, and the residue was purified by silica gel column chromatography (benzene/acetone=8/1) to give 80 mg of the desired compound.

Rf: 0.44 (benzene/acetone=4/1),
Mass: 929 (M30),
$[\alpha]_D^{23}$: −47.5° (c 0.44, MeOH),
UV: $\lambda_{max}^{MeOH}$ 281 nm, $E_{1cm}^{1\%}=205$,
Molecular formula: $C_{45}H_{72}NO_{14}Br$.

EXAMPLE 9

23-Deoxy-23-bromo-4″-O-isovaleryl-YO- 9010

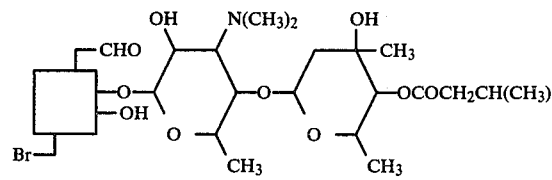

72.7 mg of 23-bromo-2′-O-acetyl-4″-O-isovaleryl-YO-9010 was dissolved in 5 ml of methanol, and the solution was heated under reflux for 5 hours. Methanol was evaporated under reduced pressure, and the residue was purified by silica gel column chromatography (chloroform/methanol=100/1) to give 51.2 mg of the desired compound.

Rf: 0.42 (benzene/acetone=2/1),
Mass: 887 (M+),
$[\alpha]_D^{23}$: −32.3° (c 0.347, MeOH),
UV: $\lambda_{max}^{MeOH}$ 281 nm, $E_{1cm}^{1\%}=227$,
$^1$H-NMR (CDCl₃): δ0.97 (6H, d, CH(CH₃)₂), 1.81 (3H, s, 12—CH₃), 2.49 (6H, s, N(CH₃)₂), 5.78 (1H, d, H-13), 6.27 (1H, d, H-10), 7.29 (1H, d, H-11), 9.67 (1H, s, CHO).

EXAMPLE 10

23,2′-Di-O-acetyl-4″-O-isovaleryl-YO-9010

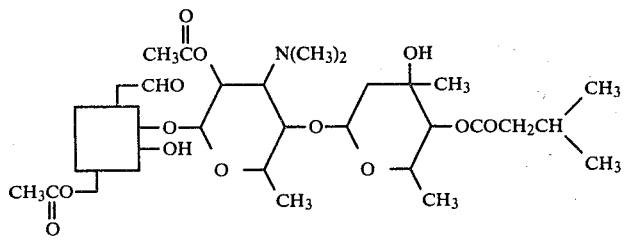

0.9 g of 23,2'-di-O-acetyl-YO-9010 (prepared in accordance with Example 10 of the specification of Japanese Laid-Open Patent Publication No. 31699/1982) was dissolved in 3 ml of pyridine, and 3 ml of isovaleric anhydride was added. The mixture was stirred at 8° C. for 48 hours. The reaction mixture was poured into 50 ml of ice water to decompose the excess of isovaleric anhydride. Then, it was extracted with 100 ml of toluene. The toluene layer was washed with two 50 ml portions of a saturated aqueous solution of sodium bicarbonate and then with an aqueous solution of sodium chloride, and dried over anhydrous sodium sulfate. Anydrous sodium sulfate was removed by decantation, and the residue was purified by silica gel column chromatography (benzene/acetone=8/1) to give 212.3 mg of the desired product.

Rf: 0.44 (benzene/acetone=4/1),
Mass: 909 (M+),
$[\alpha]_D^{23}$: −52.7° (c 0.16, MeOH),
UV: $\lambda_{max}^{MeOH}$ 281 nm, $E_{1cm}^{1\%}=223$,
Molecular formula: $C_{47}H_{75}NO_{16}$.

EXAMPLE 11

4"-O-isovaleryl-YO-9010 and 23-O-acetyl-4"-O-isovaleryl-YO-9010

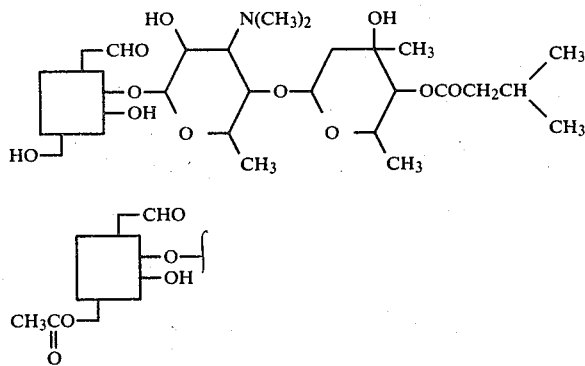

190 mg of 23,2'-di-O-acetyl-4"-O-isovaleryl-YO-9010 was dissolved in 15 ml of methanol, and the solution was heated under reflux for 6 hours.

After cooling, the solvent was evaporated, and the residue was treated in 40% ammonia-saturated methanol at room temperature for 2 hours. The reaction mixture was poured into 20 ml of water, and extracted with 50 ml of chloroform. The chloroform layer was washed with aqueous sodium chloride solution, and dried over anhydrous sodium sulfate. The solvent was evaporated under reduced pressure, and the residue was purified by silica gel column chromatography (benzene/acetone=5/1 and 4/1) to give 15.6 mg of 23O-acetyl-4"-O-isovaleryl-YO-9010 and 64.4 mg of 4"-O-isovalery-YO-9010.

23-O-Acetyl-4"-O-isovaleryl-YO-9010
Rf: 0.53 (benzene/acetone=2/1),
Mass: 867 (M+),
$[\alpha]_D^{23}$: −36.7° (c 0.193, MeOH),
UV: $\lambda_{max}^{MeOH}$ 282 nm, $E_{1cm}^{1\%}=226$,
Molecular formula: $C_{45}H_{73}NO_{15}$.

4"-O-isovaleryl-YO-9010
Rf: 0.33 (benzene/acetone=2/1),
Mass: 825 (M+),
$[\alpha]_D^{23}$: −45.4° (c 0.348, MeOH),
UV: $\lambda_{max}^{MeOH}$ 282 nm, $E_{1cm}^{1\%}=236$,
Molecular formula: $C_{43}H_{71}NO_{14}$.

EXAMPLE 12

23-O-tosyl-YO-9010

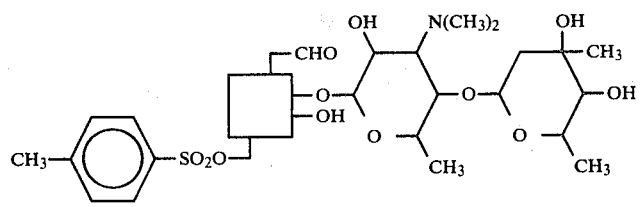

300 mg of YO-9010 was dissolved in 5 ml of methylene chloride, and 386 mg of tosyl chloride and 0.262 ml of pyridine were added. The mixture was stirred at room temperature for 3 hours. The reaction mixture was poured into 50 ml of an aqueous solution of sodium bicarbonate, and extracted with 50 ml of chloroform.

The chloroform layer was washed with two 50 ml portions of aqueous sodium chloride solution and dried over anhydrous sodium sulfate. The dried product was purified by silica gel column chromatography (benzene/acetone=3/1) to give 93 mg of the desired compound.

Rf: 0.56 (chloroform/methanol=7/1)
Mass: 895 (M+),
$[\alpha]_D^{22}$: −27° (c 0.923, MeOH),
UV: $\lambda_{max}^{MeOH}$ 280 nm, $E_{1cm}^{1\%}$=231,
$\lambda_{max}^{MeOH}$ 226 nm, $E_{1cm}^{1\%}$=158.
Molecular formula: $C_{45}H_{69}NO_{15}S$.

EXAMPLE 13

23-O-tetrahydropyranyl-YO-9010

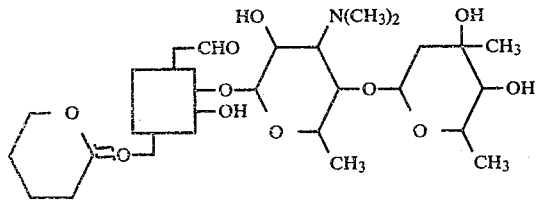

200 mg of YO-9010 was dissolved in 5 ml of methylene chloride, and the solution was cooled to 0° C. To the solution were added 0.0725 ml of 2,3-dihydro-4H-pyran and 0.06 ml of trifluoroacetic acid. The mixture was stirred at 8° C. for 24 hours, and then at room temperature for 6 hours. The reaction mixture was poured into 50 ml of ice water, and extracted with 50 ml or 10 ml of chloroform. The chloroform layer was washed with 50 ml of an aqueous solution of sodium chloride and dried over anhydrous sodium sulfate. After filtration, chloroform was removed by concentration, and the residue was purified by silica gel column chromatography (chloroform/methanol=50/1 to 45/1) to give 64.7 mg of the desired compound.

Rf: 0.65 (CHCl₃/MeOH=7/1),
Mass: 825 (M+),
$[\alpha]_D^{22}$: −41.2° (c 0.885, MeOH),
UV: $\lambda_{max}^{MeOH}$ 283 nm, $E_{1cm}^{1\%}$=250,
Molecular formula: $C_{43}H_{71}NO_{14}$.

EXAMPLE 14

23-Deoxy-23-bromo-YO-9010 dimethylacetal

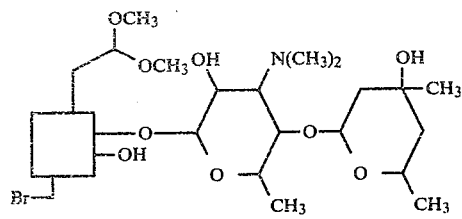

200 mg of 23-deoxy-23-23-bromo-YO-9010 was dissolved in 9.17 ml of 0.25% HCl-methanol, and the solution was stirred at room temperature for 1 hour. The reaction mixture was poured into 50 ml of chloroform, washed with an aqueous solution of sodium bicarbonate, and dried over anhydrous sodium sulfate. The dried product was filtered, and concentrated to dryness to give 208 mg of the desired compound. This compound can be used for the next reaction without further purifying it.

Rf: 0.54 (CHCl₃/MeOH=6/1),
Mass: 849 (M+),
Molecular formula: $C_{40}H_{68}NO_{13}Br$,
¹H-NMR (CDCl₃): δ1.80 (3H, s, 12—CH₃), 2.47 (6H, s, N(CH₃)₂), 3.21 (3H, s, OCH₃), 3.26 (3H, s, OCH₃), 5.74 (1H, d, H-13), 6.23 (1H, d, H-10), 7.22 (1H, d, H-11).

EXAMPLE 15

23-Deoxy-23-methylthio-YO-9010 dimethylacetal

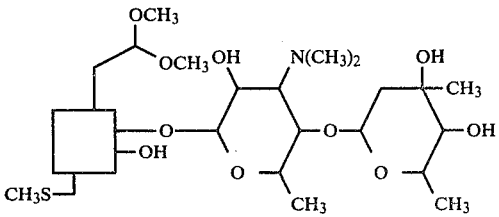

150 mg of 23-bromo-YO-9010 dimethylacetal and 0.1 ml of an aqueous solution of NaSMe (20–25%) were dissolved in 3 ml of acetone, and the solution was stirred at room temperature for 3 hours. The reaction mixture was poured into 50 ml of chloroform, washed with 50 ml of a saturated aqueous solution of sodium bicarbonate and 50 ml of aqueous sodium chloride solution, and then dried over anhydrous sodium sulfate. The product was decanted and, then concentrated to dryness. The residue was purified by silica gel column chromatography to give 104.7 mg of the desired compound.

Rf: 0.42 (chloroform/methanol/conc. aqueous ammonia=15/1/0.1)
Mass: 817 (M+),
$[\alpha]_D^{23}$: +7.95° (c 1.28, MeOH),
UV: $\lambda_{max}^{MeOH}$ 285 nm, $E_{1cm}^{1\%}$=246,
Molecular formula: $C_{41}H_{71}NO_{13}S$.

EXAMPLE 16 23-Deoxy-23-methylthio-YO-9010

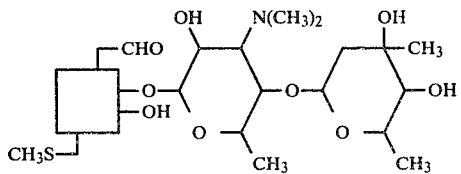

90 mg of 23-methylthio-YO-9010 dimethylacetal was dissolved in 1 ml of acetonitrile, and 10 ml of 0.05N-HCl was added. The mixture was allowed to stand at 13° C. for 4 hours. The pH was adjusted to 9, and the reaction mixture was extracted with 30 ml of chloroform. The chloroform layer was washed with aqueous sodium chloride solution, and dried over anhydrous sodium sulfate. Anhydrous sodium sulfate was removed by decantation. The residue was concentrated under reduced pressure, and then purified by silica gel column chromatography (chloroform/methanol=35/1 and 15/1) to give 20.9 mg of 23-deoxy-23-methylthio-YO-9010 and 18.4 mg of 23-deoxy-23-methylthiodemycarosyl-YO-9010.

23-Deoxy-23-methylthio-YO-9010,
Rf: 0.36,
Mass: 771 (M+),
$[\alpha]_D^{23}$: +3.46° (c 1.04, MeOH),
UV: $\lambda_{max}^{MeOH}$ 285 nm, $E_{1\ cm}^{1\%}$=218,
Molecular formula: $C_{39}H_{65}NO_{12}S$.

EXAMPLE 17

23-Deoxy-23-phthalimide-YO-9010

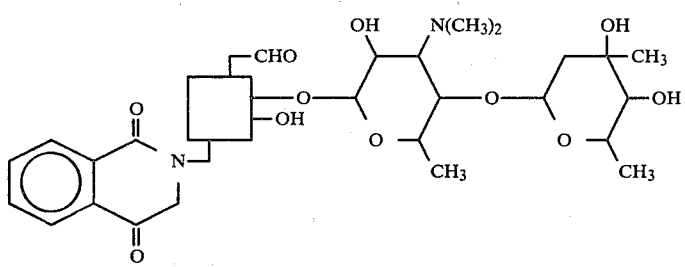

500 mg of 23-deoxy-23-bromo-YO-9010 was dissolved in 2 ml of DMF, and 550 mg of phthalimide potassium was added. The mixture was stirred at room temperature for 20 hours. The reaction mixture was poured into 20 ml of water, extracted with three 30 ml portions of chloroform, and dried over anhydrous sodium sulfate. After filtration, chloroform was removed by concentration, and the residue was purified by silica gel column chromatography (CHCl₃/MeOH=15/1) and Sephadex LH-20 (MeOH) column chromatography to give 70.5 mg of the desired compound.

Rf: 0.72 (CHCl₃/MeOH=7/1),
Mass: 870 (M+),
$[\alpha]_D^{22}$: +35.7° (c 0.959, MeOH),
UV: $\lambda_{max}^{MeOH}$ 282 nm, $E_{1\ cm}^{1\%}$ =243, $\lambda_{max}^{MeOH}$ 241 nm, $E_{1\ cm}^{1\%}$ =133, $\lambda_{max}^{MeOH}$ 220 nm, $E_{1\ cm}^{1\%}$ =471,
Molecular formula: $C_{46}H_{66}N_2O_{14}$.

EXAMPLE 18

23-Deoxy-23-phenylthio-YO-9010

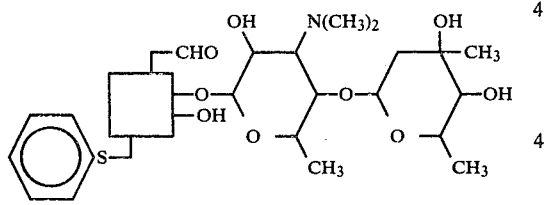

200 mg of 23-deoxy-23-bromo-YO-9010 and 66 mg of sodium thiophenolate were dissolved in a mixed solvent consisting of 10 ml of acetonitrile and 5 ml of water. The solution was stirred at room temperature for 1 hour. The reaction mixture was poured into 20 ml of water, and extracted with 20 ml of benzene. The benzene layer was washed with 20 ml of aqueous sodium chloride solution, and dried over anhydrous sodium sulfate. Benzene was removed by concentration, and the residue was purified by silica gel column chromatography (benzene/acetone=4/1) to give 15 mg of the desired compound.

Rf: 0.74 (CHCl₃/MeOH=7/1),
Mass: 833 (M+),
$[\alpha]_D^{23}$: +63.6° (c 0.896, MeOH),
UV: $\lambda_{max}^{MeOH}$ 284 nm, $E_{1\ cm}^{1\%}$=254,
Molecular formula: $C_{44}H_{67}NO_{12}S$.

EXAMPLE 19

23-Deoxy-23-morpholino-YO-9010

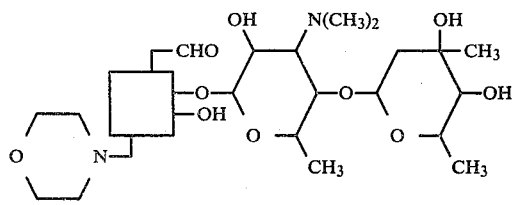

100 mg of 23-deoxy-23-bromo-YO-9010 and 93 mg of NaI were dissolved in 2 ml of DMF, and 0.136 ml of morpholine was added. The solution was stirred at room temperature for 22.5 hours. The reaction mixture was poured into 50 ml of ice water, and extracted with 50 ml of chloroform. The chloroform layer was washed with 30 ml of an aqueous solution of sodium bicarbonate and two 30 ml portions of aqueous sodium chloride solution, and dried over anhydrous sodium sulfate. The chloroform layer was concentrated and purified by silica gel column chromatography (CHCl₃/MeOH=40/1) to give 28 mg of the desired compound.

Rf: 0.70 (CHCl₃/MeOH=7/1),
Mass: 810 (M+),
$[\alpha]_D^{23}$: −8.0° (c 0.980, MeOH),
UV: $\lambda_{max}^{MeOH}$ 285 nm, $E_{1\ cm}^{1\%}$=229,
Molecular formula: $C_{42}H_{70}N_2O_{13}$.

EXAMPLE 20

23-O-mandelyl-YO-9010

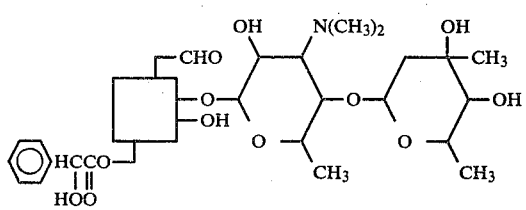

150 mg of 23-deoxy-23-bromo-YO-9010 and 223 mg of NaI were dissolved in 4 ml of DMSO, and 370 mg of sodium mandelate was added. The mixture was stirred at room temperature for 2 days. The reaction mixture was poured into 50 ml of water, extracted with two 50 ml portions of chloroform, washed with aqueous sodium chloride solution, and dried over anhydrous sodium sulfate. After filtration, the solvent was evaporated under reduced pressure, and the residue was purified by silica gel column chromatography (CHCl₃/MeOH=40/1 and 35/1) to give 29 mg of the desired compound.

Rf: 0.33 (chloroform/methanol=10/1),
Mass: 875 (M+),
$[\alpha]_D^{22}$: −33.5° (c 0.511, MeOH), UV: $\lambda_{max}^{MeOH}$ 282 nm, $E_{1\ cm}^{1\%}$ =223,
Molecular formula: $C_{46}H_{69}NO_{15}$.

EXAMPLE 21

23-Deoxy-23-thiocyanato-YO-9010

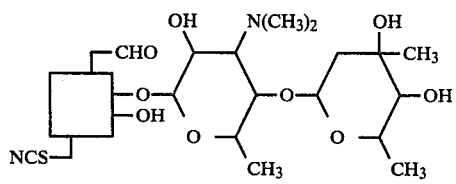

100 mg of 23-deoxy-23-bromo-YO-9010 was dissolved in 5 ml of acetonitrile, and 80 mg of sodium thiocyanate was added. The mixture was stirred at 60° C. for 1 hour. The reaction mixture was poured into 30 ml of chloroform, washed with two 30 ml portions of aqueous sodium chloride solution, and dried over anhydrous sodium sulfate. After filtration, the product was purified by silica gel column chromatography (benzene/acetone=3/1) to give 70 mg of the desired compound.

Rf: 0.52 (benzene/acetone=$\frac{1}{2}$),
Mass: 782 (M+),
$[\alpha]_D^{23}$: −8.1° (c 0.36, MeOH),
UV: $\lambda_{max}^{MeOH}$ 281 nm, $E_{1\ cm}^{1\%}$ =254,
Molecular formula: $C_{39}H_{62}N_2O_{12}S$.

EXAMPLE 22

23-Deoxy-23-bromo-2′-O-acetyl-4″-O-phenylthioacetyl-YO-9010

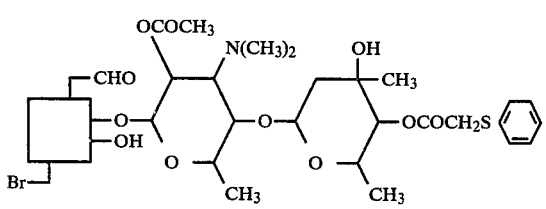

540 mg of phenylthioacetic acid was dissolved in 2 ml of methylene chloride, and 0.446 ml of triethylamine and 0.395 ml of pivaloyl chloride were added. The mixture was stirred at room temperature for 30 minutes. Then, 388 mg of 23-deoxy-23-bromo-2′-O-acetyl-YO-9010, 0.37 ml of pyridine and 3.5 ml of methylene chloride were added to the mixture, and the mixture was further stirred at room temperature for 6 hours. The reaction mixture was poured into 30 ml of water, and extracted with 30 ml of chloroform. The chloroform layer was washed with a saturated aqueous solution of sodium bicarbonate and an aqueous solution of sodium chloride, and dried over anhydrous sodium sulfate. The dried product was filtered and concentrated, and the residue was purified by silica gel column chromatography (benzene/acetone=10/1 and 9/1) to give 145 mg of the desired compound.

Rf: 0.49 (benzene/acetone=3/1),
Mass: 996 (M+),
$[\alpha]_D^{23}$: −33.5° (c 0.475, MeOH),
UV: $\lambda_{max}^{MeOH}$ 280 nm, $E_{1\ cm}^{1\%}$ =207,
Molecular formula: $C_{48}H_{70}NO_{14}SBr$.

EXAMPLE 23

23-O-benzyl-2′-O-acetyl-YO-9010

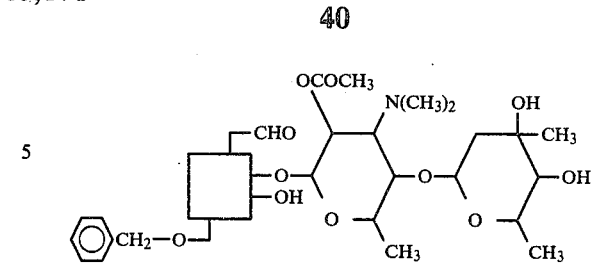

150 mg of 2′-O-acetyl-YO-9010 was dissolved in 3 ml of benzyl bromide, and 60 mg of silver oxide was added. The mixture was stirred at 40° to 50° C. for 6 hours. After cooling, the reaction mixture was filtered. The residue was purified by silica gel column chromatography (benzene/acetone=6/1) to give 34 mg of the desired compound.

Rf: 0.46 (benzene/acetone=2/1),
Mass: 873 (M+),
$[\alpha]_D^{22}$: −55.15° (c 1.1, MeOH),
UV: $\lambda_{max}^{MeOH}$ 284 nm, $E_{1\ cm}^{1\%}$ =219,
Molecular formula: $C_{47}H_{71}NO_{14}$.

EXAMPLE 24

23-O-benzyl-YO-9010

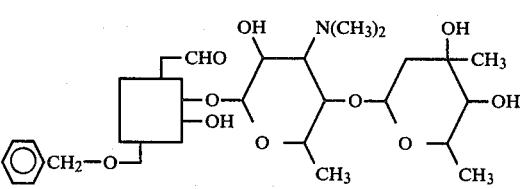

33 mg of 23-O-benzyl-2′-O-acetyl-YO-9010 was dissolved in 10 ml of methanol, and the solution was heated under reflux for 8 hours. After cooling, the solvent was evaporated, and the residue was purified by silica gel column chromatography (chloroform/methanol=40/1) to give 22 mg of the desired compound.

Rf: 0.47 (chloroform/methanol=7/1),
Mass: 831 (M+),
$[\alpha]_D^{23}$: −42.9° (c 1.035, MeOH),
UV: $\lambda_{max}^{MeOH}$ 283 nm, $E_{1\ cm}^{1\%}$ =238,
molecular formula: $C_{45}H_{69}NO_{13}$.

EXAMPLE 25

23-Deoxy-23-bromo-4″-O-phenylthioacetyl-YO-9010

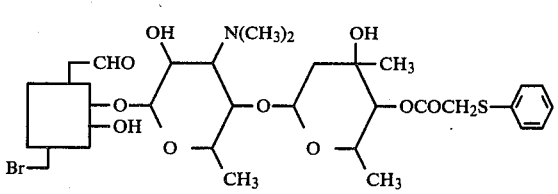

124 mg of 23-deoxy-23-bromo-2′-O-acetyl-4″-O-phenylthioacetyl-YO-9010 was dissolved in 5 ml of methanol, and the solution was heated under reflux for 6 hours. After cooling, methanol was evaporated, and the residue was purified by silica gel column chromatography (benzene/acetone=5/1) to give 31 mg of the desired compound.

Rf: 0.43 (benzene/acetone=2/1),
Mass: 954 (M+),
$[\alpha]_D^{23}$: −22.1° (c 0.362, MeOH), UV: $\lambda_{max}^{MeOH}$ 281 nm, $E_{1\ cm}^{1\%} = 203$,
Molecular formula: $C_{46}H_{68}NO_{13}SBr$.

EXAMPLE 26

3,2'-Di-O-acetyl-4''-O-isovaleryl-YO-9010

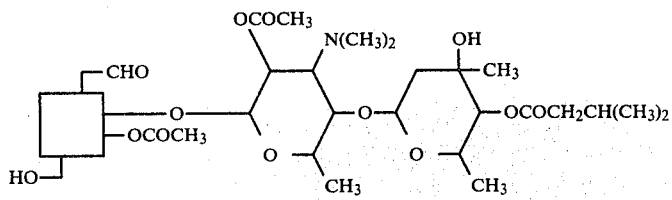

0.9 g of N-1 substance (3-O-acetyl-4''-O-isovaleryl-YO-9010) was dissolved in 20 ml of methylene chloride, and the solution was cooled with ice. Then, 0.197 ml of acetic anhydride was added, and the mixture was stirred under ice cooling for 1 hour and then at room temperature for 1 hour. The reaction mixture was poured into an aqueous solution of sodium bicarbonate, and extracted with 100 ml of toluene. The toluene layer was washed with aqueous sodium chloride solution and dried over anhydrous sodium sulfate. After filtration, the solvent was evaporated under reduced pressure. The residue was dried to give 0.9 g of the desired compound. This compound can be used in the next reaction without further purifying it.

Rf: 0.36 (benzene/acetone = 2/1),

EXAMPLE 27

3,2'-Di-O-acetyl-23-O-methyl-4''-O-isovaleryl-YO-9010

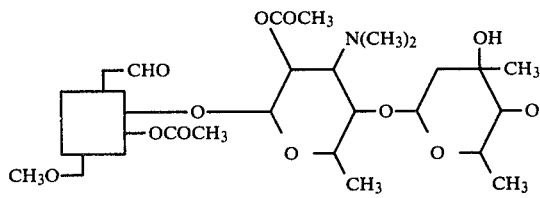

150 mg of 3,2'-di-O-acetyl-4''-O-isovaleryl-YO-9010 was dissolved in 4 ml of methyl iodide, and 80 mg of Ag$_2$O was added. The mixture was heated under reflux for 6 hours. After cooling, the reaction mixture was filtered, and methyl iodide was evaporated under reduced pressure. The residue was purified by silica gel column chromatography (benzene/acetone = 8/1) to give 46.3 mg of the desired compound.

Rf: 0.74 (benzene/acetone = 2/1),
Mass: 923 (M+),
$[\alpha]_D^{23}$: $-47.9°$ (c 1.1, MeOH),
UV: $\lambda_{max}^{MeOH}$ 282 nm, $E_{1\ cm}^{1\%} = 223$,
Molecular formula: $C_{48}H_{77}NO_{16}$.

EXAMPLE 28

3-O-Acetyl-23-O-methyl-4''-O-isovaleryl-YO-9010

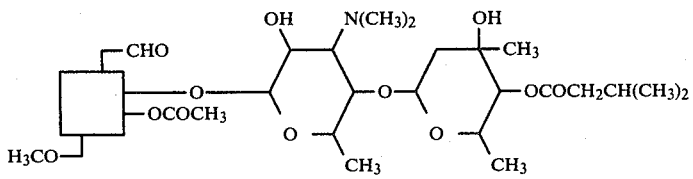

46 mg of 3,2'-di-O-acetyl-23-O-methyl-4''-O-isovaleryl-YO-9010 was dissolved in 10 ml of methanol, and the solution was heated under reflux for 7 hours. After cooling, methanol was evaporated under reduced pressure. The residue was purified by silica gel column chromatography (benzene/acetone = 4/1) to give 40 mg of the desired compound.

Rf: 0.50 (benzene/acetone = 2/1),
Mass: 881 (M+),
$[\alpha]_D^{23}$: $-31.8°$ (c 1.075, MeOH),
UV: $\lambda_{max}^{MeOH}$ 283 nm, $E_{1\ cm}^{1\%} = 221$,
Molecular formula: $C_{46}H_{75}NO_{15}$.

What is claimed is:

1. A compound of the following general formula:

(I)

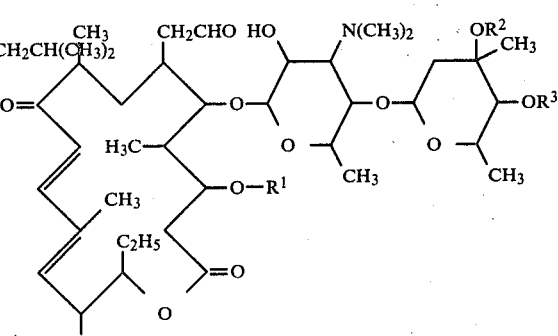

wherein
R$^1$ and R$^2$ represent a hydrogen atom or a lower alkanoyl group having 2 to 6 carbon atoms;
R$^3$ represents a hydrogen atom or the group —COCH$_2$R$^5$ in which R$^5$ represents a lower alkyl group having 1 to 4 carbon atoms or an aryl or pyridyl group bonded through a sulfur atom;

$R^4$ represents a lower alkyl group having 1 to 4 carbon atoms, an aryl methyl group, pyridyl methyl group, a hydronyl lower alkyl group having 1 to 4 carbon atoms, an aryl group, a nitrile group, a 5- or 6-membered heterocyclic group having 1 to 4 hetero atoms selected from nitrogen and sulfur atoms, a tetrahydropyranyl group or a 6-methoxytetrahydropyran-2-yl group;

A represents the group —O— or —S—, or A and $R^4$, taken together, represent a halogen atom or a nitrile group, or a pharmaceutical acceptable salt thereof.

2. A compound of claim 1 wherein $R^1$ represents a hydrogen atom or an acetyl group, $R^2$ represents a hydrogen atom, and $R^4$—A— represents a halogen atom.

3. A compound of claim 2 wherein $R^1$ represents a hydrogen atom or an acetyl group, $R^2$ represents a hydrogen atom, $R^3$ represents a hydrogen atom or an isovaleryl group, and $R^4$—A— represents a halogen atom.

4. A compound of claim 3 which is 23-bromo-23-demycinosyloxytylosin.

5. A compound of claim 3 which is 23-iodo-23-demycinosyloxytylosin.

6. A compound of claim 3 which is 2'-O-acetyl-4"-O-isovaleryl-23-bromo-23-demycinosyloxytylosin.

7. A compound of claim 3 which is 4"-O-(4-pyridyl)-thioacetyl-23-bromo-23-demycinosyloxytylosin.

* * * * *